United States Patent [19]

Tóth et al.

[11] Patent Number: 5,077,043

[45] Date of Patent: Dec. 31, 1991

[54] *HYPHANTRIA CUNEA* SEX PHEROMONES AND ATTRACTANT COMPOSITIONS INCLUDING THE PHEROMONES

[75] Inventors: Miklós Tóth, Budapest, Hungary; Hans-Rudolf Buser, Wädenswil; Heinrich Arn, Wollerau, both of Switzerland; Kenji Mori, Tokyo, Japan; Yasuo Ninomiya, Osaka, Japan; Tetsuo Omata, Osaka, Japan; Shuji Senda, Osaka, Japan; Tadashi Takeuchi; Masakazu Aburatani, both of Takaoka, Japan

[73] Assignees: Nitto Denko Co. Ltd., Ibaraki; Fuji Yakuhin Kogyo Kabushiki Kaisha, Takaoka, both of Japan

[21] Appl. No.: 535,637

[22] Filed: Jun. 11, 1990

[51] Int. Cl.$^5$ .................. A01N 25/00; C07D 303/00
[52] U.S. Cl. ...................................... 424/84; 549/512; 568/448; 568/420
[58] Field of Search ...................... 549/512; 568/448; 424/84

[56] References Cited

U.S. PATENT DOCUMENTS

| | | | |
|---|---|---|---|
| 3,888,888 | 6/1975 | Pallos et al. | 549/512 |
| 3,975,409 | 8/1976 | Eiter | 549/512 |
| 4,146,609 | 3/1979 | Ritter | 424/84 |
| 4,345,084 | 8/1982 | Chan et al. | 568/448 |
| 4,376,058 | 3/1983 | Boden et al. | 549/512 |
| 4,380,658 | 4/1983 | Boden et al. | 549/512 |
| 4,503,259 | 3/1985 | Boden et al. | 549/512 |
| 4,610,876 | 9/1986 | Underhill et al. | 424/84 |
| 4,929,441 | 5/1990 | Flint et al. | 424/84 |

FOREIGN PATENT DOCUMENTS 2933749 3/1981 Fed. Rep. of Germany.

OTHER PUBLICATIONS

Journal of Chemical Ecology, vol. 8, No. 2, "Sex Pheromone of the Fall Webworm Moth", pp. 383, 396, 1982.

*Primary Examiner*—C. Warren Ivy
*Assistant Examiner*—Amelia A. Owens
*Attorney, Agent, or Firm*—Armstrong, Nikaido, Marmelstein, Kubovcik & Murray

[57] ABSTRACT

The present invention provides mainly (3Z,6Z)-cis-9,10-epoxy-1,3,6-heneicosatriene (formula 1) and (3Z, 6Z)-cis-9,10-epoxy-1,3,6-elcosatriene (formula 2) which are *Hyphantria cunea* sex pheromones. The invention provides attractant components having high attraction effect for *Hyphantria cunea*, that is, *Hyphantria cumea* sex pheromones having high attraction activity and the intermediates which can selectively synthesize such pheromones with great ease.

Furthermore, the invention provides attractant compositions with high attraction effect for *Hyphantria cunea* including such above noted pheromones.

Consequently, this invention is completed.

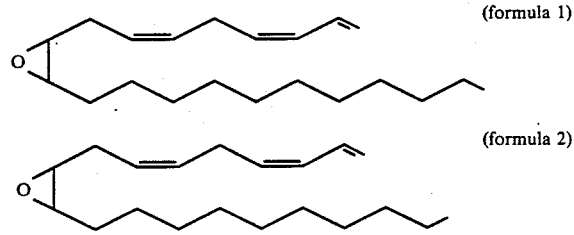

14 Claims, 2 Drawing Sheets

HYPHANTRIA CUNEA SEX PHEROMONES AND ATTRACTANT COMPOSITIONS INCLUDING THE PHEROMONES

INDUSTRIAL FIELD OF THE INVENTION

The present invention relates to *Hyphantria cunea* sex pheromones and intermediates for their synthesis and atractant compositions including the pheromones.

The object of the invention is to provide attractant components having high attraction effect for *Hyphantria cunea*, that is, *Hyphanria cunea* sex pheromones having high attraction activity and the intermediates which can selectively synthesize such pheromones with great ease and the attractant compositions having high attraction effect for *Hyphantria cunea*.

BACKGROUND OF THE INVENTION

*Hyphantria cunea*, whose original home is North America, causes various damages to trees, farms and fruits by their baiting in many countries of the world such as the United States, the Soviet Union, Europe etc. The common name for *Hyphantria cunea* is "Fall webworm".

In Japan, just after the world war II, larvae of *Hyphantria cunea* eating pulatanus were found in Tokyo at first.

After this finding, the authority of Japanese Goverment tried to perfectly remove them from Japan at early stage.

It was impossible to prevent the increasing of their distribution; consequently they are found not only in the Kanto area but also in the Kansai area and the Tohhoku area.

Up to date, they are widely distributed in Japan mainly centered in town areas, which cause damage to large amounts of street trees.

It was investigated to use sex pheromones for protecting and removing *Hyphantria cunea*, and cooperative research was advanced for analyzing the structures of the sex pheromones by scholars of the United States and the Soviet Union.

At 1982, W. L. Roelofs et al reported that (9Z,12Z)-9,12-octadecadien-1-al (formula 4), (9Z,12Z,15Z)-9,12,15-octadecatrien-1-al (formula 5) and (3Z,6Z)-cis-9,10-epoxy-3,6-heneicosadiene (formula 6) were sex pheromones of *Hyphantria cunea* (A. S. Hill, B. G. Kovalev, L. N. Nikolaeva, W. L. Roelofs, J. Chem. Ecol. 8, 383 (1982)).

Though, the attractant test for *Hyphantria cunea* using above the 3 components was carried out in Japan and Europe, the attaction effect was very weak, so that it was impossible to make practical for the attractant compositions by using as traps to catch *Hyphantria cunea*.

The present inventors made a study earnestly to create attractant components having high attraction effect for *Hyphantria cunea*, that is, *Hyphantria cunea* sex pheromones having high attraction activity, furthermore the attractant compositions including such above pheromones with high attraction effect for *Hyphantria cunea*.

DETAILED DESCRIPTION OF THE INVENTION

*Hyphantria cunea* sex pheromones relating to this invention are (3Z,6Z)-cis-9,10-epoxy-1,3,6-heneicosatriene (formula 1) and (3Z,6Z)-cis-9,10-epoxy-1,3,6-eicosatriene (formula 2).

(formula 1)

(formula 2)

The physical properties of (3Z,6Z)-cis-9,10-epoxy-1,3,6-heneicosatriene (formula 1) are followings; the melting point is 14°~15° C., the refractive index with sodium D light ray at 16° C. is 1.4781, and the specific rotation, $[\alpha]^{16}_D$ with sodium D light ray of (3Z,6Z,9S,10R)-cis-9,10-epoxy-1,3,6-heneicosatriene (formula 1a) as the (9S,10R) enantiomer of heneicosatriene is −0.41° (c=1.97, in CHCl₃).

(formula 1a)

The physical properties of (3Z,6Z)-cis-9,10-epoxy-1,3,6-eicosatriene (formula 2) are followings; the melting point is 2°~3° C., the refractive index with sodium D light ray at 16° C. is 1.4787, and the specific rotation, $[\alpha]^{16}_D$ with sodium D light ray at 16° C. of (3Z,6Z,9S,10R)-cis-9,10-epoxy-1,3,6-eicosatriene (formula 2a) as the (9S,10R) enantiomer of eicosatriene is −0.41° (c=1.23, in CHCl₃).

(formula 2a)

In the first place, the present inventors have confirmed that (3Z,6Z)-cis-9,10-epoxy-1,3,6-heneicosatriene (formula 1) and (3Z,6Z)-cis-9,10-epoxy-1,3,6-eicosatriene (formula 2) were real *Hyphantria cunea* sex pheromones by the following procedures.

Larvae of *Hyphantria cunea* were gathered and reared from larvae to pupae.

The ovipositor tips of one hundred adult *Hyphantria cunea* females being selected from the 2 days old metamorphosed females were taken out, and their pheromones are extracted with hexane (1~5 μl per 1 female).

Continuously, the extraction obtained by above the process was identified according to the following manner.

First, the gas chromatograph analysis was operated on a SE54 column with a flame ionization detector (FID) and an electro antenographic detector (EAD).

The operation of gas chromatograph analysis was carried out on condition of maintaining at 40° C. for 2 minutes then raising up to 140° C. by 20° C./min and further raising up to 225° C. by 5° C./min.

Figure 1:
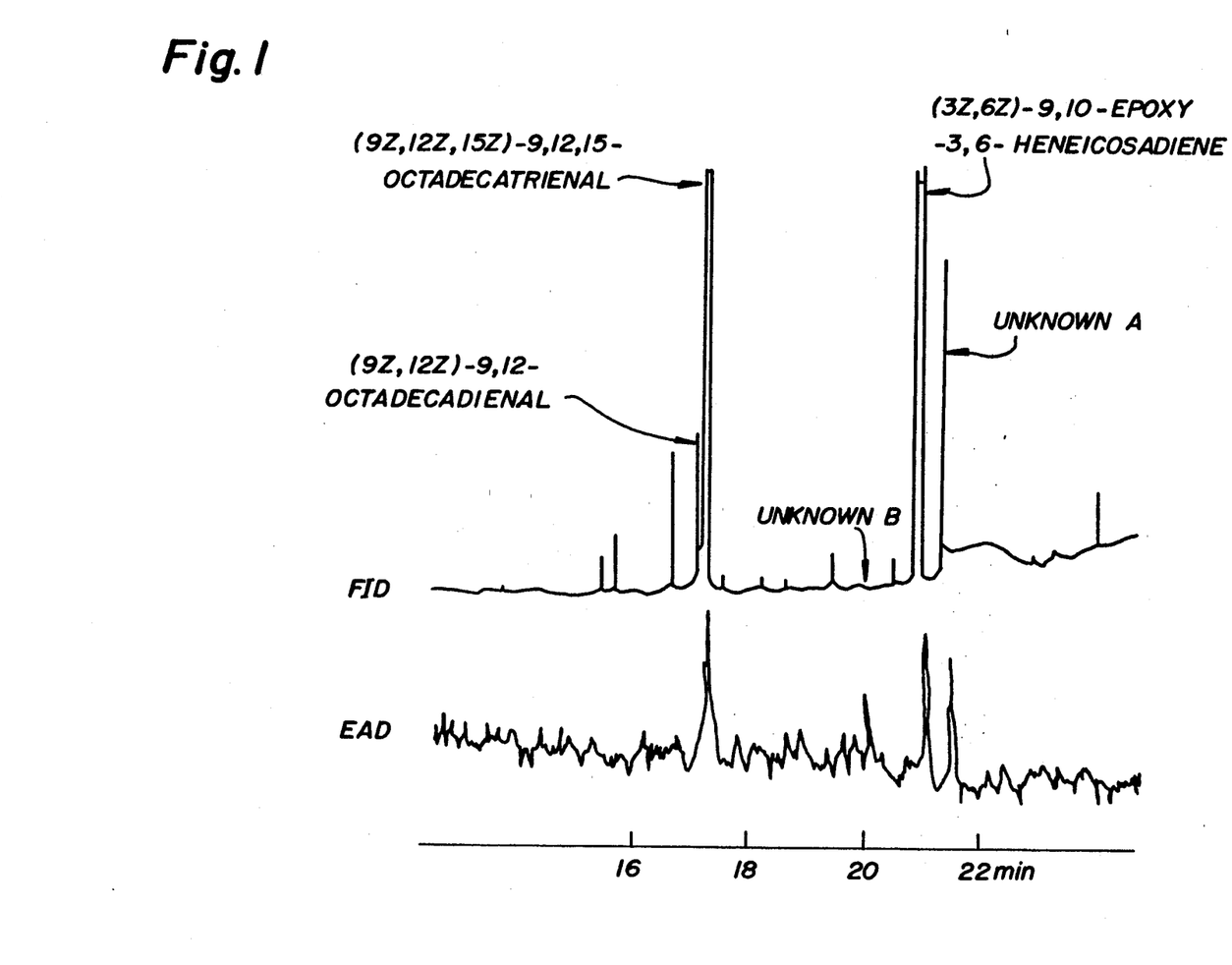
FIG. 1 is the gas chromatograph of the extraction of ovipositor of *Hyphantria cunea* females with a flame ionization (FID) and an electro antenographic detecter (EAD).

The results are shown in FIG. 1.

By the gas chromatograph with the electro antenographic detector (EAD), the presence of 5 biologically active components are analyzed.

Furthermore, each fraction separated by gas chromatography was subjected to mass spectrometry, i.e., GC-MS analysis.

The operation of GC-MS analysis (Finnigan 4023, EI, 50eV) was carried out on a SE54 with a program of maintaining at 50° C. for 2 minutes, then raising up to 140° C. by 20° C./min and further raising up to 280° C. by 5° C./min.

Subsequently, 3 components in 5 biologically active components were known sex pheromone of *Hyphantria cunea* which were (9Z,12Z)-9,12-octadecadien-1-al (formula 4), (9Z,12Z,15z)-9,12,15-octadecatrien-1-al (formula 5) and (3Z,6Z)-cis-9,10-epoxy-3,6-heneicosadiene (formula 6).

Furthermore, the identification of the two unknown biologically active components A and B (see FIG. 1) was conducted as follows.

The unknown component A was subjected to gas chromatograph analysis and measured 2289 in RI by the electro antenographic detector (EAD).

Figure 2:
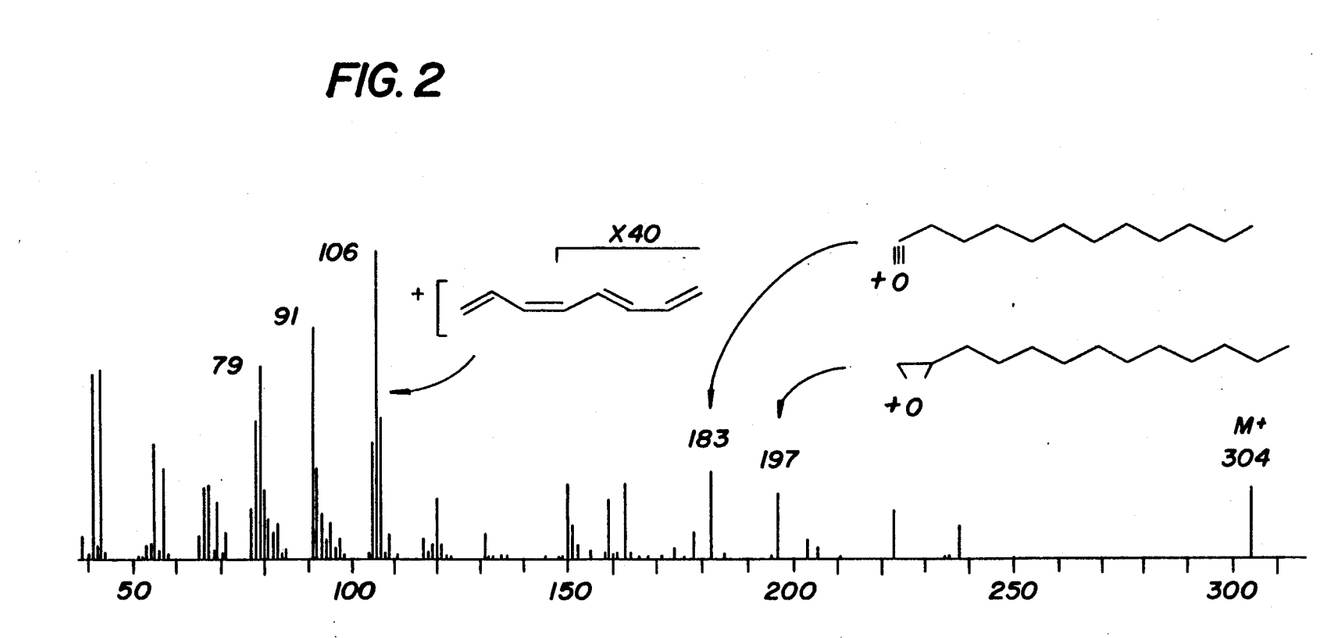
FIG. 2 is the chart by mass spectric analysis of (3Z,6Z)-cis-9,10-epoxy-1,3,6-eicosatriene (formula 2).

The mass spectrum of the unknown component A showed a molecular ion peak at m/e 304 with a series of highly unsaturated ion peaks at m/e 79, 91 and 106 (see FIG. 2).

On the other hand, the mass spectrum of (3Z,6Z)-cis-9,10-epoxy-3,6-heneicosadiene (formula 6) showed ion peaks at m/e 79, 93 and 108, suggesting a terminal double bond of the unknown component A.

Also ion peaks at m/e 183 and 197 suggested the presence of epoxy groups in 9 and 10 positions.

Moreover, the retension difference between the unknown component A and (3Z,6Z)-9,10-epoxy-3,6-heneicosadiene (formula 5) was the same as between (3Z,6Z,9Z)-1,3,6,9-nonadecatetraene and (3Z,6Z,9Z)-3,6,9-nonadecatriene, and suggesting double bond conjugation of the unknown component A.

In order to test the above hypothesis, (3Z,6Z,9Z)-1,3,6,9-nonadecatetraene was epoxidized with m-chloroperbenzoic acid.

This reaction mixture was subjected to gas chromatograph analysis with the electro antenographic detector (EAD) and the results showed that the mixture contained three components.

One of the above components indicated highly active to the male *Hyphantria cunea*.

Furthermore, the mass spectrum of this component gave a molecular ion peak at m/e 276 and ion peaks at m/e 79, 91 and 106, thus suggesting the unknown component A is the $C_{21}$ homologue.

The physical properties of the unknown component A are identical with those of (3Z,6Z)-cis-9,10-epoxy-1,3,6-heneicosatriene (formula 1).

Thus, the unknown component A is confirmed to be (3Z,6Z)-cis-9,10-epoxy-1,3,6-heneicosatriene (formula 1).

(3Z,6Z)-cis-9,10-epoxy-1,3,6-heneicosatriene (formula 1) obtained by separation and purification had a yeild of 8 ng per 1 female *Hyphantria cunea*.

The unknown component B is identified in the same manner as above.

The unknown component B is subjected to gas chromatograph analysis and measured 2185 in RI by the electro antenographic detector (EAD).

Furthermore, the mass spectrum of the unknown component B shows a molecular ion peak m/e 260 and a highly unsaturated compound ion peaks at m/e 79, 91 and 106.

Furthermore, the physical properties of the unknown B are identical with those of (3Z,6Z)-cis-9,10-epoxy-1,3,6-eicosatriene (formula 2).

Moreover, a component comprising (9S,10R) eicosatriene isolated from the unknown component B measured for specific rotation with sodium D light ray at 16° C., which is identical with that of (3Z,6Z)-cis-9,10-epoxy-1,3,6-eicosatriene (formula 2).

Thus, the unknown component B is confirmed to be the $C_{20}$ homologue, which is (3Z,6Z)-cis-9,10-epoxy-1,3,6-eicosatriene (formula 2).

(3Z,6Z)-cis-9,10-epoxy-1,3,6-eicosatriene (formula 2) obtained by separation and purification had a yield of 0.04 ng per 1 female *Hyphantria cunea*.

The activities are measured by means of the electro antenographic detector (EAD) of (3Z,6Z)-cis-9,10-epoxy-1,3,6-heneicosatriene (formula 1) and (3Z,6Z)-cis-9,10-epoxy-1,3,6-eicosatriene (formula 2) comprising the (9S,10R) enantiomer, i.e., (3Z,6Z,9S,10R)-cis-9,10-epoxy-1,3,6-heneicosatriene (formula 1a), and (3Z,6Z,9S,10R)-cis-9,10-epoxy-1,3,6-eicosatriene (formula 2a), respectively.

The results shows that (3Z,6Z)-cis-9,10-epoxy-1,3,6-heneicsatriene (formula 1) and (3Z,6Z)-cis-9,10-epoxy-1,3,6-eicosatriene (formula 2) both with (9S,10R) heneicosatriene and eicosatriene are more active to the antenna of male *Hyphantria cunea* than with (9R,10S) heneicosatriene and eicosatriene.

Accordingly, it is indicated that every component consist of S form in 9-position and the R-form in 10-position exhibit higher biological activities.

(formula 1a)

(formula 2a)

The above results reveal that the components both (3Z,6Z)-cis-9,10-epoxy-1,3,6-heneicosatriene (formula 1) and (3Z,6Z)-cis-9,10-epoxy-1,3,6-eicosatriene (formula 2) are biologically active pheromones, and that (3Z,6Z,9S,10R)-cis-9,10-epoxy-1,3,6-heneicosatriene (formula 1a) and (3Z,6Z,9S,10R)-cis-9,10-epoxy-1,3,6-eicosatriene (formula 2a) are pheromones especially higher in biological activities.

The compounds (3Z,6Z)-cis-9,10-epoxy-1,3,6-heneicosatriene (formula 1) and (3Z,6Z)-cis-9,10-epoxy-1,3,6-eicosatriene (formula 2) are much easier to synthesize from (5Z,8Z)-cis-2,3-epoxy-5,8,10-undecatrien-1-ol (formula 3).

(formula 3)

Stated more specifically, (5Z,8Z)-cis-2,3-epoxy-5,8,10-undecatrien-1-ol (formula 3) is allowed to react with tosylchloride (p-toluenesulfonyl chloride) in a pyridine solvent to prepare (3Z,6Z)-cis-9,10-epoxy-1,3,6-undecatrienyl tosylate (formula 7), thereafter which is purified and reacted with lithium di(n-decyl)-cuprate in an ether solvent at low temperature.

On completion of the reaction, the after-treatment was effected in accordance with the usual manner and the resultant was purified using a silica gel chromatography to give (3Z,6Z)-cis-9,10-epoxy-1,3,6-heneicosatriene (formula 1).

These steps are showned in followings.

(formula 1)

(5Z,8Z)-cis-2,3-epoxy-5,8,10-undecatrien-1-ol (formula 3) is treated to prepare (3Z,6Z)-cis-9,10-epoxy-1,3,6-undecatrienyl tosylate (formula 7) in the same manner as the above, thereafter which is reacted with lithium di(n-decyl) cuprate to prepare (3Z,6Z)-cis-9,10-epoxy-1,3,6-eicosatriene (formula 2), then after-treatment and purification are needed in the same manner as the above.

These steps are showed in followings.

In these steps, (3Z,6Z,9S,10R)-cis-9,10-epoxy-1,3,6-heneicosa triene (formula 1a) or (3Z,6Z,9S,10R)-cis-9,10-epoxy-1,3,6-eicosatriene (formula 2a) is obtained by using (5Z,8Z)-cis-2,3-epoxy-5,8,10-undecatrien-1-ol (formula 3) being the (2R,3S) triene, i.e., (2R,3S,5Z,8Z)-cis-2,3-epoxy-5,8,10-undecatrien-1-ol (formula 3a).

(formula 3a)

Furthermore, (3Z,6Z,9R,10S)-cis-9,10-epoxy-1,3,6-heneicosatriene (formula 1b) or (3Z,6Z,9R,10S)-cis-9,10-epoxy-1,3,6-eicosatriene (formula 2b) is obtained by using (5Z,8Z)-cis-2,3-epoxy-5,8,10-undecatrien-1-ol (formula 3) being the (2S,3R) triene, i.e., (2S,3R,5Z,8Z)-cis-2,3-epoxy-5,8,10-undecatrien-1-ol (formula 3b).

(formula 3b)

(formula 1b)

(formula 2b)

The component (5Z,8Z)-cis-2,3-epoxy-5,8,10-undecatrien-1-ol (formula 3) can be obtained by following the steps 1 to 10.

The step 8

(formula 3)

The step 9

(formula 19)

The step 10

(formula 3)

Hereinafter, the detailed explanation from the step 1 to 10 are described.

THE STEP 1

In brief of this step, the diyne compound (formula 10) is prepared from 1,4-dichloro-2-butyne (formula 8) which is allowed to react with the anion of propargyl alcohol derivative (formula 9) in the presence of copper salt.

The amount of the anion of propargyl alcohol derivative is to be desirably used 1~1.1 equivalent weight to the amount of 1,4-dichloro-2-butyne (formula 8).

The monovalent copper salt is used the necessary amount for catalyst.

The amount of copper (I) chloride is to be favorably used 0.01~0.2 equivalent weight to the amount of 1,4-dichloro-2-butyne.

It is preferable that this process is carried out with the ether system solvent especially tetrahydrofuran.

It is the desirable reaction temperature at 0°~50° C. in the case of 1,4-dichloro-2-butyne (formula 8) being to react with the anion of propargyl alcohol derivative.

In this step, 1,7-bis-(2-tetrahydropyranyloxy)-2,5,8-decatriene produced as by-products is to be separated by the silica gel chromatography.

THE STEP 2

In brief in this step, the triyne compound (formula 12) is prepared from the diyne compound (formula 10) which is allowed to react with dianion of 3-butyn-1-ol (formula 11) in the presence of copper salt.

The amount of the dianion in 3-butyn-1-ol (formula 11) is desirably used at 1.0~2.5 equivalent weight to the amount of diyne compound (formula 10).

The monovalent copper salt is to be used at an amount necessary for catalyst activity.

The amount of copper (I) chloride is favorably 0.1~0.5 equivalent weight to the amount of diyne compound (formula 10).

This step is preferably proceeding in a solvent, the ether system solvent especially tetrahydrofuran.

It is the desirable reaction temperature at 20°~70° C. in the case of diyne compound (formula 10) wherein it is allowed to react with anion of 3-butyn-1-ol (formula 11).

THE STEP 3

In brief, the triene compound (formula 13) is prepared from the triyne compound (formula 12) by catalytic reduction with hydrogen gas in the presence of the catalyst and quinoline.

As for the reducing catalyst used in this step, P-2 nickel, Lindlar catalyst, palladium hold on carrier, for example, calcium sulfate or barium sulfate is preferable example.

The amount of the catalyst is favorably 0.1~0.3 equivalent weight to the amount of triyne compound (formula 12).

This reaction is preferably conducted in a solvent selected from the ester system solvent like as ethyl acetate, the alcoholic system solvent like as methanol, ethanol or the ether system solvent like as tetrahydrofuran, dioxane etc.

As for desirable condition, the hydrogen pressure is 1.0~1.2 atm and the reaction temperature is 0°~40° C.

THE STEP 4

In brief, in this step the mesylate compound (formula 15) is prepared from the triene compound (formula 13) which is allowed to react with methanesulfonyl chloride (formula 14) in the presence of the amine.

The amount of methanesulfonyl chloride (formula 14) is favorably 1.0~2.0 equivalent weight to the amount of triene compound (formula 13).

The amine favorable for using in the present invention is triethylamine, pyridine and the amount of above amine is favorably 1.5~3.0 equivalent weight to the amount of triene compound (formula 13).

This reaction is preferably conducted in a solvent selected from the halogen system solvent like methylene chloride, chloroform or the ether system solvents like tetrahydrofuran, dioxane etc.

It is desirable that the reaction temperature is —20°~20° C.

THE STEP 5

In brief, in this step the bromide compound (formula 16) is prepared from the mesylate compound (formula 15) which is allowed to react with a bromination agent.

In this step, a bromination agent favorably used is lithium bromide, sodium bromide, or the like.

The amount of the bromination agent is favorable 1.5~5.0 equivalent weight to the amount of mesylate compound (formula 15).

It is preferable that this step is carried out in the presence of the mild basic salt, for example, sodium hydrogen carbonate is favorable 0.5~2.0 equivalent weight to the amount of mesylate compound (formula 15).

This step is preferable conducted in a solvent selected from the ether system solvent such as tetrahydrofuran, dioxane etc.

THE STEP 6

In brief, in this step the tetraene compound (formula 17) is prepared from the bromide compound (formula 16) which is allowed to react with an alkaline compound.

The alkaline compound favorably used in this step is selected from sodium hydroxide, potassium hydroxide, lithium hydroxide etc.

The amount of the above alkaline compounds is favorably used 2.0~10 equivalent weight to the amount of bromide compound (formula 16).

This step is preferably conducted in a solvent selected from the alcoholic system solvent like methanol, ethanol, isopropyl alcohol or the mixture of the above alcoholic system solvents in any proportions etc.

It is preferable that the reaction temperature is 30°~70° C.

THE STEP 7

In brief, in this step the tetraene alcoholic compound (formula 18) is prepared from the tetraene compound (formula 17) which is allowed to react with an acidic compound as same amount of the catalyst in the solvent.

The acidic compound favorable used in this step is tosylic acid, pyridinium para-toluenesulfonate, acetic acid, hydrochloric acid or the like.

The solvent favorably used in this step is selected from the alcoholic system solvents like methanol, ethanol, the alcoholic mixing solvent which was mixed with water or alcoholic system solvent in any proportions etc.

It is preferable that the reaction temperature is 10°~50° C.

THE STEP 8

In brief, in this step the epoxy-alcoholic compound of (5Z,8Z)-cis-2,3-epoxy-5,8,10-undecatrien-1-ol (formula 3) in high optical purity is prepared from tetraene alcoholic compound (formula 18) carried out by the asymmetric epoxidation by Sharpress et al. (T. Katsuki, K. B. Sharpress, J. Am. Chem. Soc., 102, 5947(1980).

The amount of titanium isopropoxide is favorably 0.2~2.0 equivalent weight to the amount of tetraene alcoholic compound (formula 18) in this step.

The amount of the type of molecular seives 4A to be favorably used is 0.5~2.0 equivalent weight to the amount of tetraene alcoholic compound (formula 18).

The completion of this reaction can be accelerated by the addition of type of molecular seives 4A.

In this step, D-(−)-diethyl tartrate is used in the case of (2R,3S,5Z,8Z)-cis-2,3-epoxy-5,8,10-undecatrien-1-ol (formula 3b) being synthesized and L-(+)-diethyl tartrate is used in the case of (2S,3R,5Z,8Z)-cis-2,3-epoxy-5,8,10-undecatrien-1-ol (formula 3b) being synthesized.

The amount of dietyl tartrate is to be favorable used 1.2~2.0 equivalent weight to the amount of tetraene alcoholic compound (formula 18).

The amount of tert-butyl hydroperoxide is favorably 1.2~2.0 equivalent weight to the amount of tetraene alcoholic compound (formula 18).

It is preferable that the reaction temperature is —10°~30° C.

The optical purity of epoxy alcoholic compound (formula 3) in this step is 80~90% e.e, though a slightly different purity may be found owing to the amount of titanium isopropoxide, reaction temperature, the time required for the completion of this reaction, etc.

The optical purity of epoxy alcoholic compound (formula 3) is determined by high-performance liquid chromatography analysis of the ester derivative with (−)-camphanic acid.

THE STEP 9

In brief, in this step the optically pure 3,5-dinitro-benzoate compound (formula 19) is recrystallized from crude 3,5-dinitro-benzoate derived with 3,5-dinitrobenzoly chloride and pyridine from the optical active epoxy the alcoholic compound (formula 3) which is obtained by above asymmetric epoxidation reaction of Sharpress.

The solvent used for recrystallization of 3,5-dinitrobenzoate compound (formula 19) is favorably exampled in the aliphatic hydrocarbon system solvents like n-hexane, n-pentane for example, the ether system solvent like diethyl ether, tetrahydrofuran or the mixture of any of the above solvents in any proportion etc.

THE STEP 10

In brief, in this step the optically pure epoxy alcoholic compound (formula 3) as described (5Z,8Z)-cis-2,3-epoxy-5,8,10-undecatrien-1-ol (formula 3) is prepared from the optically pure 3,5-dinitrobenzoate compound (formula 19) decomposed with methanol in the presence of the alkaline compound which is equal to the amount of the catalyst.

The alkaline compound favorably used in this step is for example sodium carbonate, sodium hydroxide, potassium hydroxide or the like.

The amount of above alkaline compound favorably used is 0.05~0.5 equivalent weight to the amount of 3,5-dinitrobenzoate compound (formula 19).

It is preferable that the reaction temperature is —10°~10° C.

After completion of the reaction, through the extraction, the concentration and the purification using by a silica gel chromatography, the optically pure (5Z,8Z)-cis-2,3-epoxy-5,8,10-undecatrien-1-ol (formula 3) is obtained.

The optical purity of (5Z,8Z)-cis-2,3-epoxy-5,8,10-undecatrien-1-ol (formula 3) is determined by high performance liquid chromatography analysis of the ester derivative with (−)-camphanic acid.

Hereinafter, this inventional *Hyphantria cunea* attractant compositions are described.

Either (3Z,6Z)-cis-9,10-epoxy-1,3,6-heneicosatriene (formula 1) or (3Z,6Z)-cis-9,10-epoxy-1,3,6-eicosatriene (formula 2) can be used as attractant for a capture by itself.

However, if above attractants and known *Hyphantria cunea* sex pheromones are used together at the same time, their capture effect may be expected to be greater.

In *Hyphantria cunea* attractant compositions of the present invention, all three kinds of known sex pheromones are not necessary to use together; furthermore, all (3Z,6Z)-cis-9,10-epoxy-1,3,6-heneicosatriene (formula 1) and (3Z,6Z)-cis-9,10-epoxy-1,3,6-eicosatriene (formula 2) as this inventional *Hyphantria cunea* sex pheromones are not necessary to use together, however it is favorable that (3Z,6Z)-cis-9,10-epoxy-1,3,6-heneicosatriene (formula 1) is included at least one.

The embodiments of this invention are described in following examples concerning some of the compounds of this invention: (3Z,6Z)-cis-9,10-epoxy-1,3,6-heneicosatriene (formula 1), (3Z,6Z)-cis-9,10-epoxy-1,3,6-eicosatriene (formula 2) and (5Z,8Z)-cis-2,3-epoxy-5,8,10-undecatrien-1-ol (formula 3).

Furthermore, *Hyphantria cunea* attractant compositions of the present invention are described with reference to the following tests and comparative tests.

EXAMPLE

EXAMPLE 1

The present Example 1 illustrates the method of producing (3Z,6Z,9S,10R)-cis-9,10-epoxy-1,3,6-heneicosatriene from (2R,3S,5Z,8Z)-cis-2,3-epoxy-5,8,10-undecatrien-1-ol.

(2R,3S,5Z,8Z)-cis-2,3-epoxy-5,8,10-undecatrien-1-ol(0.59 g) was solved in pyridine (14 ml), and tosylchloride(0.94 g) was added to the solution under cooling with ice.

The mixture was stirred for 15 hours at 0° C.

The reaction mixture was poured into the iced water, from which an extrative layer was separated with ether.

The layer of ether was washed by a saturated solution of copper sulfate, a saturated solution of salt in order, and it was dried by magnesium sulfate; thereafter it was concentrated.

The concentrated substance was purified by silica gel chromatography (35 g of silica gel, n-pentane/ether 5:1) to give the reaction product.

The reaction product was 3010, 1595, 1360, 1190, 1175, 970, 810 (cm$^{-1}$) in IR spectrum which was measured by using film method for preparing samples.

As the above result, it is confirmed that the reaction product is (2R,3S,5Z,8Z)-cis-2,3-epoxy-5,8,10-undecatrienyltosylate.

The yield amount of reaction product was 0.95 g, the yield rate 87%.

The obtained (2R,3S,5Z,8Z)-cis-2,3-epoxy-5,8,10-undecatrienyltosylate (284 mg) was dissolved in ether (7 ml), and the solution was dropped into a solution of lithium di(n-decyl) cuprate in ether (0.75M, 3,4 ml) at $-60°$ C. in a stream of argon.

Then the reaction mixture was stirred for 30 min. at 60° C., and it was poured into a saturated solution of ammonium chloride.

Furthermore, it was stirred for 30 min, the stirred mixture was filtrated, the filtrate was separated from a layer of organic substance and a layer of water, thereafter an extractive layer was separated with ether from the layer of water.

The mixture of the layer of organic substance and the extractive layer of ether from the layer of water was washed with water, a saturated solution of salt in order, and it was dried by magnesium sulfate; thereafter it was concentrated.

The concentrated substance was purified by silica gel chromatography (40 g of silica gel, n-pentane/ether 50:1) to give the reaction product.

The reaction product was measured by mass spectrometry.

The result showed that the molecular weight of reaction product was 304.2744, molecular formula was $C_{21}H_{36}O$(F.W.=304.2766).

The IR spectrum peak for the reaction product were 3090, 3020, 2960, 2930, 2860, 1640, 1590, 1460, 1430, 1380, 1260, 995, 900, 720 (cm$^{-1}$).

The measurement was carried out by using film method for preparing samples.

Moreover, the $\delta$ amount (ppm) of proton nuclear magnetic resonance ($^1$H-NMR) spectrum were 0.88 (t;J=6.8 Hz, 3H), 1.18~1.55 (m;20H), 2.18~2.29 (m;1H), 2.40 (dt;J=6.0, 14.4 Hz, 1H), 2.88~3.00 (m;4H), 5.13 (dd;J=7.0, 17.0 Hz,1H), 5.22 (dd;J=2.0, 17.0 Hz,1H),5.41 (dd;J=8.0, 18.0 Hz, 1H), 5.45~5.57 (m;2H),6.03(deformed t;J=11.0 Hz, 1H), 6.65(dddd;J=1.1, 10.0, 11.0, 17.0 Hz,1H).

The measurement was carried out by dissolving the samples in chloroform-d, and by using 400 MHz of proton nuclear magnetic resonance ($^1$H-NMR) spectrum.

Further, the melting point of the reaction product was 14°~15° C. the reflective index with sodium D light ray at 16° C. was 1.4781, the specific rotation with sodium D light ray at 16° C.; $[\alpha]^{16}_D$ was $-0.41°$ (C=1.97, in CHCl$_3$).

As the above results, it is confirmed that the reaction product was (3Z,6Z,9S,10R)-cis-9,10-epoxy-1,3,6-heneicosatriene.

The yield amount of reaction product was 199 mg, the yield rate 77%.

EXAMPLE 2

The present Example 2 illustrates the method of producing (3Z,6Z,9Z,10R)-cis-9,10-epoxy-1,3,6-eicosatriene from (2R,3S,5Z,8Z)-cis-2,3-epoxy-5,8,10-undecatrien-1-ol.

(2R,3S,5Z,8Z)-cis-2,3-epoxy-5,8,10-undecatrienyltosylate(184 mg) obtained in the same manner as example 1 was dissolved in ether(5 ml), which was dropped into a solution of lithium di(n-nonyl) cuprate in ether (0.72M, 2.3 ml) at $-60°$ C. in a stream of argon, thereafter it was stirred for 30 min.

The reaction mixture was purified in the same manner as Example 1 to give the reaction product.

The reaction product was measured by mass spectrometry.

The result showed that the molecular weight of reaction product was 290.2581, the molecular formula was $C_{20}H_{34}O$(F.W.=290.2610).

The IR spectrum peak of the reaction product wer 3090, 3020, 2960 2930, 2860, 1640, 1590, 1460, 1430, 1380, 1260, 995, 900, 720 (cm$^{-1}$).

The measurement was carried out by using film method of preparing samples.

Moreover, the $\delta$ amount (ppm) of proton nuclear magnetic resonance ($^1$H-NMR) spectrum were 0.88 (t;J=6.8 Hz, 3H),1.18~1.55 (m;18H), 2.18~2.29 (m;1H), 2.40 (dt;J=6.0, 14.4 Hz, 1H),2.88~3.00 (m;4H), 5.13 (dd;J=7.0, 17.0 Hz,1H), 5.22 (dd;J=2.0, 17.0 Hz,1H), 5.41 (dd;J=8.0, 18.0 Hz,1H), 5.45~5.57

(m;2H), 6.03 (deformed t; J=11.0 Hz, 1H), 6.65 (dddd;J=1.1, 10.0, 11.0, 17.0 Hz,1H).

The measurement was carried out by dissolving the samples in chloroform-d, and by using 400 MHz of proton nuclear magnetic resonance ($^1$H-NMR) spectrum.

Further, the melting point of the reaction product was 2°~3° C., the reflective index with sodium D light ray at 16° C. was 1.4787, the specific rotation with sodium D light ray at 16° C.; $[\alpha]^{16}_D$ was −0.57° (C=1.23, in CHCl$_3$).

As the above results, it is confirmed that the reaction product was (3Z,6Z,9S,10R)-cis-9,10-epoxy-1,3,6-eicosatriene.

The yield amount of reaction product was 109 mg, the yield rate 68%.

EXAMPLE 3

The present Example 3 illustrates the method of producing (3Z,6Z,9R,10R)-cis-9,10-epoxy-1,3,6-eicosatriene from (2S,3R,5Z,8Z)-cis-2,3-epoxy-5,8,10-undecatrien-1-ol.

(2S,3R,5Z,8Z)-cis-2,3-epoxy-5,8,10-undecatrienyltosylate(0.78 g) was obtained from (2S,3R,5Z,8Z)-cis-2,3-epoxy-5,8,10-undecatrien-1-ol (0.47 g) in the same manner as Example 1.

The IR spectrum of it was as same as (2R,3S,5Z,8Z)-cis-2,3-epoxy-5,8,10-undecatrienyltosylate which was obtained at Example 1.

Further the obtained (2S,3R,5Z,8Z)-cis-2,3-epoxy-5,8,10-undecatrienyltosylate(240 mg) was treated in the same manner as Example 1 to give the reaction product.

The mass spectrum, the IR spectrum, the proton nuclear magnetic resonance ($^1$H-NMR) spectrum, the melting point, the reflective index with sodium D light ray at 16° C. of the reaction product was as same as (3Z,6Z,9S,10R)-cis-9,10-epoxy-1,3,6-heneicosatriene which was obtained at Example 1.

But the specific rotation with sodium D light ray at 16° C.; $[\alpha]^{16}_D$ was +0.43° (C=2.39, in CHCl$_3$).

As the above results, it is confirmed that the reaction product was (3Z,6Z,9R,10S)-cis-9,10-epoxy-1,3,6-eicosatriene.

The yield amount of reaction product was 164 mg.

EXAMPLE 4

The present Example 4 illustrates the method for producing (3Z,6Z,9R,10S)-cis-9,10-epoxy-1,3,6-eicosatriene from (2S,3R,5Z,8Z)-cis-2,3-epoxy-5,8,10-undecatrien-1-ol.

The (2S,3R,5Z,8Z)-cis-2,3-epoxy-5,8,10-undecatrienyltosylate (147 mg) was treated in the same manner as Example 2 to give the reaction product.

The mass spectrum, the IR spectrum, the proton nuclear magnetic resonance ($^1$H-NMR) spectrum, the melting point, the reflactive index with sodium D light ray at 16° C. of the reaction product was as same as (3Z,6Z,9S,10R)-cis-9,10-epoxy-1,3,6-eicosatriene which was obtained at Example 2.

But the specific rotation with sodium D light ray at 16° C.; $[\alpha]^{16}_D$ was +0.62° (C=2.34, in CHCl$_3$).

As the above results confirmed that the reaction product was (3Z,6Z,9R,10S)-cis-9,10-epoxy-1,3,6-eicosatriene.

The yield amount of the reaction product was 95 mg, the yield rate 74%.

EXAMPLE 5

The present Example 5 illustrates the method of producing (2R,3S,5Z,8Z)-cis-2,3-epoxy-5,8,10-undecatrien-1-ol.

THE STEP 1

3-(tetrahydropyranyloxy)-1-propyne (58.9 g) was dissolved in tetrahydrofuran in a stream of argon, which was dropped into a solution of ethylmagnesium bromide in tetrahydrofuran (2.0M, 210 ml) at room temperature.

The mixture was stirred for 1 hour at 50° C., to which copper (I) chloride (4.1 g) was added, and stirred for 20 min. at 40° C.

Further, a solution of 1.4-dichloro-2-butyne (49.2 g) in tetrahydrofuran (100 ml) was poured into the mixture at 5° C.

The reaction mixture was heated to 40° C., and stirred for 12 hours.

Further it was cooled to room temperature, which was poured in an ammonium chloride solvent (400 ml), from which an extractive layer was separated with ether.

The layer of ether was washed by a saturated solution of salt, and it was dried by magnesium sulfate, thereafter it was concentrated.

The concentrated substance was purified by using silica gel chromatography (800 g of silica gel, n-pentane/ether 15:1) to give the reaction product.

The IR spectrum peak of the reaction product were 2300, 2230, 1120, 1025 (cm$^{-1}$).

The measurement was carried out by using film method for preparing samples.

Moreover, the δ amount (ppm) of proton nuclear magnetic resonance ($^1$H-NMR) spectrum were 1.20~2.20 (m;6H), 3.29 (t;J=2, 9 Hz, 2H),3.35~4.00(m;2H), 4.12 (t;J=2.9 Hz,2H), 4.28 (dd;J=4.7, 2.9 Hz,2H), 4.80 (m;1H).

The measurement was carried out by dissolving the samples in chloroform-d, and by using 100 MHz of proton nuclear magnetic resonance ($^1$H-NMR) spectrum.

Further, the reflective index with sodium D light ray at 19° C. was 1.5096.

As the above results, it is confirmed that the reaction product was 1-chloro-7-(2-tetrahydropyranyloxy)-2,5-heptadiyne.

The yield amount of reaction product was 52.6 g, the yield rate 58%.

THE STEP 2

3-butyn-1-ol(24.4 g) was dissolved in tetrahydrofuran(100 ml) in a stream of argon, and the solution was dropped into a solution of ethylmagnesium bromide in tetrahydrofuran (2.0M, 382.5 ml) at 20° C.

The mixture was stirred for 1 hours at 60° C., to which copper (I) chloride (7.6 g) was added, and stirred for 1 hour at 35° C.

1-chloro-7-(2-tetrahydropyranyloxy)-2,5-heptadiyne (52.6 g) was solved in tetrahydrofuran(150 ml) which was added to the stirred solution at 35° C.

Then it was stirred for 15 hours at 40° C., and for 5 hours at 60° C.

The reaction mixture was poured in a saturated solution of ammonium chloride solvent, from which an extractive layer was separated with ether.

The layer of ether was washed by a saturated solution of salt, and it was dried by magnesium sulfate, thereafter it was concentrated.

The concentrated substance was purified by using silica gel chromatography (350 g of silica gel, n-pentane/ether 1:1) to obtain the reaction product.

The IR spectrum peak of the reaction product were 3450, 2250, 1120, 1060, 1040, 1025 (cm$^{-1}$).

The measurement of it was carried out by using film method for preparing samples.

Moreover, the δ amount (ppm) of proton nuclear magnetic resonance ($^1$H-NMR) spectrum were 1.30~2.10 (m;6H), 1.91(br;OH), 2.30~2.57 (m;2H), 3.00~3.29(m;4H), 3.35~4.02(m;2H), 3.72 (t;J=6.8 Hz,2H), 4.24 (dt;J=2.3, 16.0 Hz,2H), 4.80 (m;1H).

The measurement was carried out by dissolving the samples in chloroform-d, and by using 100 MHz of proton nuclear magnetic resonance ($^1$H-NMR) spectrum.

As the above results, it is confirmed that the reaction product was 11-(2-tetrahydropyranyloxy)-3,6,9-undecatriyn-1-ol.

The yield amount of reaction product was 49.6 g.

THE STEP 3

11-(2-tetrahydropyranyloxy)-3,6,9-undecatriyn-1-ol(49.6 g) was dissolved in ethylacetate(500 ml), to which Lindlar catalyst(8.5 g) and quinoline (8 ml) were added, the mixture was stirred furiously in a stream of hydrogen.

After consumption of hydrogen stopped, the solution of reduction was filtrated, and the filtrate was concentrated.

The concentrate was dissolved in ether, which was washed with diluted hydrochloric acid, water, a saturated solution of salt in order, then the layer of ether was washed by a saturated solution of salt and dried by magnesium sulfate; thereafter it was concentrated.

The concentrated substance was purified by using silica gel chromatography (900 g of silica gel, n-pentane/ether 2:1) to give the reaction product.

The IR spectrum peak of the reaction product were 3430, 3025, 1120, 1080, 1055, 1025 (cm$^{-1}$).

The measurement was carried out by using film method for preparing samples.

Moreover, the δ amount (ppm) of proton nuclear magnetic resonance ($^1$H-NMR) spectrum were 1.10~2.10 (m;6H), 1.77(br;OH), 2.35 (dd;J=5.8, 8.7 Hz,2H), 2.50~3.10(m;4H), 3.65 (t;J=5.8 Hz,2H) 3.20~4.50(m;4H), 4.65(m;1H), 5.15~5.80 (m;6H).

The measurement was carried out by dissolving the samples in chloroform-d, and by using 100 MHz of proton nuclear magnetic resonance ($^1$-NMR) spectrum.

Further, the reflective index with sodium D light ray at 18° C. was 1.4953.

As the above results, it is confirmed that the reaction product was (3Z,6Z,9Z)-11-(2-tetrahydropyranyloxy)-3,6,9-undecatrien-1-ol.

The yield amount of reaction product was 43.9 g, the yield rate 86%.

THE STEP 4 AND THE STEP 5

(3Z,6Z,9Z)-11-(2-tetraydrophyranyloxy)-3,6,9-undecatrien-1-ol (43.9 g) was dissolved in methylene chloride (460 ml), to which triethyl amine(330 ml) was added, then the mixture was cooled with ice, thereafter in which methanesulfonyl chloride(22.7 g) was dropped.

It was stirred for 10 min., then the reaction mixture was washed with water, cold diluted hydrochloric acid, a saturated solution of sodium bicarbonate, water in order.

Further, it was dried by magnesium sulfate; thereafter it was concentrated to give a mesylate compound(57.0 g).

The obtained crude mesylate compound was dissolved in a solution of tetrahydrofuran (630 ml), and to which lithium chloride anhydride (71.7 g) and sodium bicarbonate(35.3 g) were added, then it was stirred for 18 hours.

Thereafter the reaction mixture was concentrated, and it was dissolved in ether.

The solution of ether was filtrated, and the filtrate was washed by a saturated solution of salt, and it was dried by magnesium sulfate, then it was concentrated.

The concentrated substance was purified by using silica gel chromatography (600 g of silica gel, n-pentane/ether 20:1) to give the reaction product.

The IR spectrum peak of the reaction product were 3025, 1120, 1020 (cm$^{-1}$).

The measurement of it was carried out by using film method for preparing samples.

Moreover, the δ amount (ppm) of proton nuclear magnetic resonance ($^1$H-NMR) spectrum were 1.20~2.20 (m;6H), 2.40~3.10 (m;6H), 3.38 (ddd;J=0.6, 7.0, 7.0 Hz,2H), 3.45~4.07(m;2H), 4.07~4.30(m;2H), 4.63(m;1H), 5.17~5.80 (m;6H).

The measurement was carried out by dissolving the samples in chloroform-d, and by using 90 MHz of proton nuclear magnetic resonance ($^1$H-NMR) spectrum.

Further, the reflective index with sodium D light ray at 20° C. was 1.5078.

As the above results, it is confirmed that the reduction products was (3Z, 6Z, 9Z)-1-bromo-11-(2-tetrahydropyranyloxy)-3,6,9-undecatriene.

The yield amount of reaction product was 47.3 g, the yield rate 87%.

The step 6

Potassium hydroxide (40.5 g) was dissolved in a mixture of methanol (1500 ml) and ethanol (3000 ml), to which (3Z, 6Z, 9Z)-1-bromo-11-(2-tetrahydropyranyloxy)-3,6,9-undecatriene (47.3 g) was added, and the mixture was stirred 20 min at 65° C.

The reaction mixture was concentrated, in which ether and water were poured, and it was stirred for extraction.

The layer of ether was washed by a saturated solution of salt, and it was dried by magnesium sulfate, thereafter it was concentrated.

The concentrated substance was purified by using silica gel chromatography (1100 g of silica gel, n-pentane/ether 50:1) to give the reaction product.

The IR spectrum peak of the reaction product were 3090, 3025, 1640, 1590, 1120, 1025, 905 (cm$^{-1}$).

The measurement was carried out by using film method for preparing samples.

Moreover, the δ amount (ppm) of proton nuclear magnetic resonance ($^1$H-NMR) spectrum were 1.10~2.30 (m;6H),2.60~3.10 (m;4H),3.30~4.45 (m;4H), 4.65 (m;1H),4.90~5.80(m;7H), 6.03 (dd;J=10.9, 10.9 Hz,1H), 6.68 (dt;J=10.9, 16.8 Hz,1H).

The measurement was carried out by dissolving the samples in chloroform-d, and by using 100 MHz of proton nuclear magnetic resonance ($^1$H-NMR) spectrum.

Further, the reflective index with sodium D light ray at 20° C. was 1.5021.

As the above results, it is confirmed that the reaction product was (2Z,5Z,8Z)-1-(2-tetrahydropyranyloxy)-2,5,8,10-undecatetraene.

The yield amount of reaction product was 21.1 g, the yield rate 59%.

The step 7

(2Z,5Z,8Z)-1-(2-tetrahydropyranyloxy)-2,5,8,10-undecatetraene (21.1 g) was dissolved in methanol (150 ml), to which pyridinium paratoluene sulfonate (4 g) was added, it was stirred for 24 hours at room temperature.

Then the reaction mixture was concentrated, and the concentrated substance was dissolved in ether.

The solution of ether was washed by a saturated solution of sodium bicarbonate, a saturated solution of salt in order, and it was dried by magnesium sulfate; thereafter it was concentrated.

The concentrated substance was purified by using silica gel chromatography (700 g of silica gel, n-pentane/ether 4:1) to give the reaction product.

The IR spectrum peak of the reaction product were 3350, 3040, 1640, 1590, 1000, 905 (cm$^{-1}$).

The measurement was carried out by using film method for preparing samples.

Moreover, the $\delta$ amount (ppm) of proton nuclear magnetic resonance ($^1$H-NMR) spectrum were 2.60~3.10 (m;4H),4.25 (d;J=5.5 Hz,2H), 4.90~5.85 (m;7H),6.03 (dd;J=10.9, 10.9 Hz,1H),6.68 (dddd;J=0.9, 9.8, 10.9, 16.8 Hz,1H).

The measurement was carried out by dissolving the samples in chloroform-d, and by using 100 MHz of proton nuclear magnetic resonance ($^1$H-NMR) spectrum.

Further, the reflective index with sodium D light ray at 20° C. was 1.5167.

As the above results, it is confirmed that the reaction product was (2Z,5Z,8Z)-2,5,8,10-undecatetraen-1-ol.

The yield amount of reaction product was 13.0 g, the yield rate 93%.

The step 8

In a stream of argon, titanium isopropoxide (10.6 g), D-(−)-diethyltartrate (11.5 g) were in order added to the mixture of methylene chloride (330 ml) and the type of molecular sieves 4A (9.9 g) at −23° C., and it was stirred for 30 min.

Further the solution of (2Z,5Z,8Z)-2,5,8,10-undecatetraen-1-ol (6.2 g) in methylene chloride (30 ml), and the solution of tert-butylhydroperoxide in methylene chloride (5.7M, 13.1 ml) were added to above the solution at −25° C.

Then the reaction mixture was stirred for 15 hours at −25° C., to which 10% solution of tartaric acid (190 ml) was added, held at room temperature, and it was stirred for 1 hour.

The solution of reaction mixture was separated, the layer of methylene chloride was diluted with n-hexane, then it was washed by water several times, and it was dried by magnesium sulfate; thereafter it was concentrated.

The concentrated substance was purified by using silica gel chromatography (700 g of silica gel, n-pentane/ether 5:1~3:1) to give the reaction product.

The reaction product was measured by mass spectrometry.

The result showed that the molecular weight of reaction product was 180.22, molecular formula was $C_{11}H_{16}O_2$ (F.W.=180.1150).

The IR spectrum peak of the reaction product were 3430, 3090, 3020, 1640, 1590, 1040, 905 (cm$^{-1}$).

The measurement was carried out by using film method for preparing samples.

Moreover, the $\delta$ amount (ppm) of proton nuclear magnetic resonance ($^1$H-NMR) spectrum were 1.20~1.90 (m;2H),1.90~2.70 (m;2H), 2.70~3.30 (m;2H),3.50~4.10 (m;2H),4.90~5.85 (m;5H),6.04 (dd;J=10.9, 10.9 Hz,2H), 6.65 (dddd;J=0.9, 9.8, 10.9, 16.8 Hz,1H).

The measurement was carried out by dissolving the samples in chloroform-d, and by using 100 MHz of proton nuclear magnetic resonance ($^1$H-NMR) spectrum.

Further, the reflective index with sodium D light ray at 19° C. was 1.5112, the specific rotation with sodium D light ray at 19° C.; $[\alpha]^{19}{}_D$ was +5.53° (C=0.85, in CHCl$_3$), and optical purity was 87.8% e.e.

As the above results, it is confirmed that the reaction product was (2R,3S,5Z,8Z)-cis-2,3-epoxy-5,8,10-undecatrien-1-ol.

The yield amount of reaction product was 4.1 g, the yield rate 60%.

The step 9

A solution of (2R,3S,5Z,8Z)-cis-2,3-epoxy-5,8,10-undecatrien-1-ol (3.85 g, 87.8% e.e.) in ether (85 ml) to which pyridine (24 ml) and 3,5-dinitrobenzoylchloride (6.23 g) were added under cooling with ice, and it was stirred for 12 hours at 0° C.

The reaction mixture was poured in iced water, from which an extractive layer was separated with ether.

The layer of ether was washed by a saturated solution of copper sulfate, a saturated solution of salt in order, and it was dried by magnesium sulfate, thereafter it was concentrated.

The concentrated substance was purified by recrystallizing with a solvent of n-pentane/ether (3:1~1:1) several times to give yellowish imbricate crystallization.

The IR spectrum peak of the reaction product were 3100, 3020, 1725, 1630, 1595, 1545, 1345, 1280, 1180, 910, 730, 720 (cm$^{-1}$).

The measurement was carried out by using film method for preparing samples.

Moreover, the $\delta$ amount (ppm) of proton nuclear magnetic resonance ($^1$H-NMR) spectrum were 2.10~2.65 (m;2H),2.65~3.60 (m;4H), 4.50 (d;J=6.0 Hz,1H),4.61 (d;J=4.6 Hz,1H),4.90~5.75 (m;5H), 6.00 (t;J=10.9 Hz,1H), 6.60 (dd;J=10.9, 16.8 Hz,1H).

The measurement was carried out by dissolving the samples in chloroform-d, and by using 60 MHz of proton nuclear magnetic resonance ($^1$H-NMR) spectrum.

Further, the melting point of the reaction product was 33°~33.5° C., the specific rotation with sodium D light ray at 16° C. $[\alpha]^{16}{}_D$ was +19.3° (C=0.58, in CHCl$_3$).

As the above results, it is confirmed that the reaction product was (2R,3S,5Z,8Z)-1-(3',5'-dinitrobenzoyloxy)-cis-2,3-epoxy-5,8,10-undecatriene.

The yield amount of reaction product was 1.61 g, the yield rate 20%.

The step 10

A solution of (2R,3S,5Z,8Z)-1-(3',5'-dinitrobenzoyloxy)-cis-2,3-epoxy-5,8,10-undecatriene (1.49 g) in methanol (15 ml) to which potassium carbonate (0.15 g) was added under cooling with ice, and it was stirred for 1 hour at 0° C.

The reaction mixture was concentrated, then it was diluted with water, from which an extractive layer was separated with ether.

The layer of ether was washed by water, a saturated solution of salt in order, and it was dried by magnesium sulfate, thereafter it was concentrated.

The concentrated substance was purified by using silica gel chromatography (45 g of silica gel, n-pentane/ether 4:1~2:1) to give the reaction product.

The mass spectrum, the IR spectrum, the proton nuclear magnetic resonance ($^1$H-NMR) spectrum, the reflective index with sodium D light ray at 19° C. of the reaction product was as same as (2R,3S,5Z,8Z)-cis-2,3-epoxy-5,8,10-undecatrien-1-ol which was obtained at The step 8.

But the specific rotation with sodium D light ray at 18° C.; $[\alpha]^{18}_D$ was +6.20° (C=1.66, in CHCl$_3$), and optical purity was 100% e.e.

As the above results, it is confirmed that the reaction product was (2R,3S,5Z,8Z)-cis-2,3-epoxy-5,8,10-undecatrien-1-ol.

The yield amount of reaction product was 670 mg, the yield rate 93%.

EXAMPLE 6

The present Example 6 illustrates the method for producing (2S,3R,5Z,8Z)-cis-2,3-epoxy-5,8,10-undecatrien-1-ol.

(2Z,5Z,8Z)-2,5,8,10-undecatetraen-1-ol (6.1 g) was treated in the same manner as the step 8 (Example 5) except for using L-(+)-diethyltartrate which was substituted for D-(−)-diethyltartrate to give the reaction product.

The IR spectrum, the proton nuclear magnetic resonance ($^1$H-NMR) spectrum, the reflective index with sodium D light ray at 19° C. of the reaction product was as same as (2R,3S,5Z,8Z)-cis-2,3-epoxy-2,5,8,10-undecatrien-1-ol which was obtained at The step 8.

But the specific rotation with sodium D light ray at 20° C. $[\alpha]^{20}_D$ was −5.37° (C=1.09, in CHCl$_3$), and optical purity was 89.6% e.e.

As the above results, it is confirmed that the reaction product was (2S,3R,5Z,8Z)-cis-2,3-epoxy-5,8,10-undecatrien-1-ol.

The yield amount of reaction product was 4.0 g, the yield rate 59%.

Further (2S,3R,5Z,8Z)-cis-2,3-epoxy-5,8,10-undecatriene-1-ol (3.72 g) was treated in the same manner as the step 9 (example 5) to give the reaction product.

The IR spectrum, the proton nuclear magnetic resonance ($^1$H-NMR) spectrum, the melting point of the reaction product was as same as (2R,3S,5Z,8Z)-1-(3',5'-dinitrobenzoyloxy)-cis-2,3-epoxy-5,8,10-undecatriene which was obtained at The step 9.

But the specific rotation with sodium D light ray at 13° C. $[\alpha]^{13}_D$ was −19.1° (C=1.14, in CHCl$_3$).

As the above results, it is confirmed that the reaction product was (2R,3S,5Z,8Z)-1-(3',5'-dinitrobenzoyloxy)-cis-2,3-epoxy-5,8,10-undecatriene.

The yield amount of reaction product was 1.39 g, the yield rate 18%.

Moreover (2R,3S,5Z,8Z)-1-(3',5'-dinitrobenzoyloxy)-cis-2,3-epoxy-5,8,10-undecatriene (1.24 g) was treated in the same manner as the step 10 (Example 5) to give the reaction product.

The IR spectrum, the proton nuclear magnetic resonance ($^1$H-NMR) spectrum, the reflective index with sodium D light ray at 18° C. of the reaction product was as same as (2R,3S,5Z,8Z)-cis-2,3-epoxy-5,8,10-undecatrien-1-ol which was obtained at The step 10.

But the specific rotation with sodium D light ray at 16° C.; $[\alpha]^{16}_D$ was −6.28° (C=1.95, in CHCl$_3$), and optical purity was 100% e.e.

As the above results, it is confirmed that the reaction product was (2S,3R,5Z,8Z)-cis-2,3-epoxy-5,8,10-undecatrien-1-ol.

The yield amount of reaction product was 0.55 g, the yield rate 92%.

TESTS AND COMPARATIVE TESTS

The number of caught *Hyphantria cunea* was researched by using the attractant compositions for *Hyphantria cunea* containing sex pheromones of the invention which were derived from the above Examples.

The sex pheromones combined as described in following Table 1 were involved in triangular flatter paper (the sides of triangle were severally about 2 cm length) which were adhered to adhesive plates.

The trap test was conducted at Osaka City (I: July 21, 1988, 3:00~5:00) and Ibaraki City (II: Aug. 28, 1988, 4:45~5:30, III: Aug. 29, 1988, 4:45~5:30, IV: Aug. 30, 1988, 4:45~5:30). The manner of the trap test was that the above adhesive plates were hanged in different wire nets which were put on a street tree or a street.

Results of these tests are described in following Table 1.

| Combination of various pheromones | | | | | Number of caught Hyphantria cunea | | | |
|---|---|---|---|---|---|---|---|---|
| 1 | 2 | 3 | 4 | 5 | I | II | III | IV |
| Test Example | | | | | | | | |
| ○ | ○ | ○ | ○ | ○ | 8 | 25 | 14 | 18 |
| ○ | ○ | ○ | ○ | — | 8 | 20 | 10 | 12 |
| ○ | ○ | — | ○ | — | 6 | 18 | 7 | 12 |
| Comparison | | | | | | | | |
| ○ | ○ | ○ | — | — | 1 | 4 | 2 | 1 |
| ○ | ○ | — | — | — | 0 | 2 | 1 | 0 |

Note;
1: (9Z,12Z)-9,12-octadecadienal (0.05 mg)
2: (9Z,12Z,15Z)-9,12,15-octadecatrienal (0.04 mg)
3: (3Z,6Z)-9,10-epoxy-3,6-heneicosadiene (1.05 mg)
4: (3Z,6Z)-9,10-epoxy-1,3,6-heneicosatriene (0.42 mg)
5: (3Z,6Z)-9,10-epoxy-1,3,6-eicosatriene (0.015 mg)

As the above results, it showed that the attractant compositions for *Hyphantria cunea* containing (3Z,6Z)-9,10-epoxy-1,3,6-heneicosatriene, or both (3Z,6Z)-9,10-epoxy-1,3,6-heneicosatriene and (3Z,6Z)-9,10-epoxy-1,3,6-eicosatriene of the invention resulted in the number of caught *Hyphantria cunea* to be five times higher as compared with the attractant compositions for *Hyphantria cunea* containing the known sex pheromones.

EFFECT OF THE INVENTION

As described hereinbefore, the present invention shows the following effects.

The sex pheromone for *Hyphantria cunea* of the present invention of (3Z,6Z)-9,10-epoxy-1,3,6-heneicosatriene or (3Z,6Z)-9,10-epoxy-1,3,6-eicosatriene has a high attraction effect on *Hyphantria cunea*, that is, a component of sex pheromone for *Hyphantria cunea* which has high attraction activity.

(5Z,8Z)-cis-2,3-epoxy-5,8,10-undecatrien-1-ol is an intermediate which can selectively synthesize such pheromone with great ease in order to prepare (3Z,6Z)-cis-9,10-epoxy-1,3,6-heneicosatriene or (3Z,6Z)-cis-9,10-epoxy-1,3,6-eicosatriene maintaining the absolute position as desired.

Further, the attractant compositions for *Hyphantria cunea* containing any pheromones of this invention and the known sex pheromones are the compositions with high attraction effect.

We claim:

1. An attractant composition for *Hyphantria cunea* comprising at least one of (3Z,6Z)-cis-9,10-epoxy-1,3,6-heneicosatriene (formula 1), (9Z,12Z)-9,12-octadecadien-1-al (formula 4) or (9Z,12Z,15Z)-9,12,15-octadecatrien-1-al (formula 5).

(formula 4)

(formula 5)

2. An attractant composition for *Hyphantria cunea* as set forth in claim 1, further comprising (3Z,6Z)-cis-9,10-epoxy-3,6-heneicosadiene (formula 6).

(formula 6)

3. An attractant composition for *Hyphantria cunea* as set forth in claim 1, further comprising (3Z,6Z)-cis-9,10-epoxy-1,3,6-eicosatriene (formula 2).

4. An attractant composition for *Hyphantria cunea* as set forth in claim 2, further comprising (3Z,6Z)-cis-9,10-epoxy-1,3,6-eicosatriene (formula 2).

5. An attractant compositions for *Hyphantria cunea* as set forth forth in claim 1, further comprising (3Z,6Z)-cis-9,10-epoxy-1,3,6-heneicosatriene (formula 1) as the (9S,10R) enantiomer of heneicosatriene.

6. An attractant composition for *Hyphantria cunea* as set forth in claim 2, further comprising (3Z,6Z)-cis-9,10-epoxy-1,3,6-heneicosatriene (formula 1) as the (9S,10R) enantiomer of heneicosatriene.

7. An attractant composition for *Hyphantria cunea* as set forth in claim 3, further comprising (3Z,6Z)-cis-9,10-epoxy-1,3,6-heneicosatriene (formula 1) as the (9S,10R) enantiomer of heneicosatriene.

8. An attractant composition for *Hyphantria cunea* as set forth in claim 4, further comprising (3Z,6Z)-cis-9,10-epoxy-1,3,6-heneicosatriene (formula 1) as the (9S,10R) enantiomer of heneicosatriene.

9. An attractant composition for *Hyphantria cunea* as set forth in claim 3, further comprising (3Z,6Z)-cis-9,10-epoxy-1,3,6-eicosatriene (formula 2) as the (9S,10R) enantiomer of eicosatriene.

10. An attractant composition for *Hyphantria cunea* as set forth in claim 4, further comprising (3Z,6Z)-cis-9,10-epoxy-1,3,6-eicosatriene (formula 2) as the (9S,10R) enantiomer of eicosatriene.

11. An attractant composition for *Hyphantria cunea* as set forth in claim 5, further comprising (3Z,6Z)-cis-9,10-epoxy-1,3,6-eicosatriene (formula 2) as the (9S,10R) enantiomer of eicosatriene.

12. An attractant composition for *Hyphantria cunea* as set forth in claim 10, further comprising (3Z,6Z)-cis-9,10-epoxy-1,3,6-eicosatriene (formula 2) as the (9S,10R) enantiomer of eicosatriene.

13. An attractant composition for *Hyphantria cunea* as set forth in claim 7, further comprising (3Z,6Z)-cis-9,10-epoxy-1,3,6-eicosatriene (formula 2) as the (9S,10R) enantiomer of eicosatriene.

14. An attractant composition for *Hyphantria cunea* as set forth in claim 8, further comprising (3Z,6Z)-cis-9,10-epoxy-1,3,6-eicosatriene (formula 2) as the (9S,10R) enantiomer of eicosatriene.

UNITED STATES PATENT AND TRADEMARK OFFICE
CERTIFICATE OF CORRECTION

PATENT NO. : 5,077,043
DATED : December 31, 1991
INVENTOR(S) : Miklos Toth, et al It is certified that error appears in the above-indentified patent and that said Letters Patent is hereby corrected as shown below:

On the cover page, item [75], last line, "Takaoka" should read --Toyama--.

On the cover page, item [73], first line, "Ibaraki" should read --Osaka--, last line, "Takaoka" should read --Toyama--.

Signed and Sealed this

Twentieth Day of July, 1993

Attest:

MICHAEL K. KIRK

Attesting Officer    Acting Commissioner of Patents and Trademarks